(12) United States Patent
Alleyne

(10) Patent No.: US 8,377,087 B2
(45) Date of Patent: *Feb. 19, 2013

(54) METHOD AND APPARATUS FOR SPINAL OSTEOLIGAMENTOUS RESECTION

(75) Inventor: Neville Alleyne, Oceanside, CA (US)

(73) Assignee: Elite I.P., Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/365,941

(22) Filed: Feb. 3, 2012

(65) Prior Publication Data

US 2012/0136358 A1 May 31, 2012

Related U.S. Application Data

(63) Continuation of application No. 11/757,186, filed on Jun. 1, 2007, now Pat. No. 8,109,958.

(60) Provisional application No. 60/810,540, filed on Jun. 1, 2006.

(51) Int. Cl.
*A61B 17/32* (2006.01)

(52) U.S. Cl. .......................... 606/170; 606/172; 606/180

(58) Field of Classification Search .................... None
See application file for complete search history.

(56) References Cited

U.S. PATENT DOCUMENTS

| 3,937,222 A | 2/1976 | Banko | 606/170 |
|---|---|---|---|
| 4,919,133 A | 4/1990 | Chiang | 606/159 |
| 5,201,325 A | 4/1993 | McEwen et al. | |
| 2002/0022764 A1 | 2/2002 | Smith et al. | 600/114 |
| 2002/0058958 A1 | 5/2002 | Walen | 606/170 |
| 2002/0173795 A1 | 11/2002 | Sklar | 606/80 |
| 2003/0191474 A1 | 10/2003 | Cragg et al. | 606/79 |
| 2004/0181251 A1 | 9/2004 | Hacker et al. | 606/170 |
| 2005/0165420 A1 | 7/2005 | Cha | 606/150 |
| 2005/0209610 A1 | 9/2005 | Carrison | 606/114 |

OTHER PUBLICATIONS

Braun Catalog: "Aesculap Surgical Instruments; Retraction in Perfection" Brochure C47411, Am Aesculap-Platz, 78532 Tuttlingen, Germany, www.aesculap.de.

*Primary Examiner* — Ryan Severson
*Assistant Examiner* — David Eastwood
(74) *Attorney, Agent, or Firm* — Baker Hostetler, LLP

(57) ABSTRACT

A device for osteoligamentous resection comprising a resector having a shaft with a resecting tip at its distal end, and a retractor at least partially surrounding the resector, and at least part of the retractor being moveable relative to the resector.

2 Claims, 4 Drawing Sheets

METHOD AND APPARATUS FOR SPINAL OSTEOLIGAMENTOUS RESECTION

CROSS-REFERENCE TO RELATED APPLICATIONS

This application is a continuation of U.S. patent application Ser. No. 11/757,186 entitled Method and Apparatus for Spinal Osteoligamentous Resection, filed on Jun. 1, 2007 now U.S. Pat. No. 8,109,958, which claims the benefit of U.S. Provisional Patent Application Ser. No. 60/810,540 entitled Method and Apparatus for Spinal Osteoligamentous Resection, filed on Jun. 1, 2006. The entire disclosures of application Ser. No. 11/757,186 and Application Ser. No. 60/810,540 is incorporated by reference.

BACKGROUND OF THE INVENTION

1. Field of the Invention

This invention relates to a surgical tool used in, and improved methods for, spinal canal decompression.

2. Description of the Related Art

Laminectomy is one type of surgical procedure performed to treat pain related to herniated discs, spinal stenosis and other related conditions. The goal of a laminectomy is to relieve pressure on the spinal cord or spinal nerve by widening the spinal canal. This is done by removing or trimming the lamina (roof) of the vertebrae to create more space for the nerves.

The present day multilevel decompressive laminectomy and fusions for lumbar spinal stenosis with instrumentation and bone graft requires the patient to remain in the hospital for 3 to 4 days. Some type of immobilization is generally required for anywhere from 2 to 4 months following the surgery, and it takes approximately 4 to 6 weeks of physical therapy following immobilization before the patient is capable of performing his usual daily tasks.

Such traditional open surgical procedures are being replaced with minimally invasive procedures. The limited surgical exposure that occurs with minimally invasive procedures produces less post operative pain, reduced hospital stays and faster recovery times. While minimally invasive spinal surgery and minimal access spinal surgery technology continues to provide significant advantages in spinal surgery, there continues to be a need for improved devices and techniques in this field.

SUMMARY OF THE INVENTION

Disclosed herein is a device for osteoligamentous resection comprising a resector having a shaft with a proximal end and a distal end, the distal end having a resecting tip; and a retractor having a proximal end and a distal end and having an inner surface and an outer surface, the retractor at least partially surrounding the resector, and at least part of the retractor being moveable relative to the resector. The proximal end of the retractor is preferably releasably anchorable near the proximal end of the resector, while the distal end extends beyond the distal end of the resector. Preferably, at least a portion of the inner surface of the retractor is thermally insulated and/or electrically insulated. The retractor further comprises an opening through which the resecting tip may contact tissue to be resected. In one embodiment, the retractor comprises a movable sheath.

The shape of the retractor can be concave relative to the resector near the proximal end of the resector and flat near the distal end of the resector. Alternatively, the shape of the retractor can be concave relative to the resector near the proximal end of the resector and convex relative to the resector near the distal end of the resector.

Also described herein is a device for osteoligamentous resection comprising a resector configured to resect tissue in the spinal canal region; and a retractor at least partially surrounding the resector, the retractor being configured to protect tissue in the spinal canal region from injury by the resector and configured to displace tissue near the surgical site to provide more room for performing the resection.

Also described is a device for osteoligamentous resection comprising a resector and means for retracting tissue wherein the means for retracting at least partially surrounds the resector.

Finally, there is disclosed a method for performing spinal decompression comprising exposing a resector from within a retractor, retracting tissue with said retractor, and resecting tissue with said resector.

DETAILED DESCRIPTION OF THE PREFERRED EMBODIMENT

Embodiments of the invention will now be described with reference to the accompanying Figures, wherein like numerals refer to like elements throughout. The terminology used herein is not intended to be interpreted in any limited or restrictive manner simply because it is being utilized in conjunction with a detailed description of certain specific embodiments of the invention. Furthermore, embodiments of the invention may include several novel features, no single one of which is solely responsible for its desirable attributes or which is essential to practicing the invention described herein.

Described herein is a device that is capable of performing microdissection without significantly destabilizing the spine. Generally, the surgeon first performs a minimal incision to the spine. Such an incision would provide access between the interspinous processes down through the interspinous ligament and through the area between the lamina. This would allow a portion of the ligamentum flavum or all of the ligamentum flavum to be resected. The internal decompression of both lamina and the spinal laminal junction will increase cross-sectional area within the spinal canal. With removal of bone, ligament, and synovial tissue the cross-sectional diameter within the neural foramen or in the spinal canal can be enlarged without performing a formal laminectomy or laminotomies.

The resection allows a person with severe stenosis to have improved cross-sectional diameter within a canal, making the patient less symptomatic, improving parameters such as walking distance, and minimizing the need for narcotics, anti-inflammatory medications, muscle relaxers, epidural steroids, and physical therapy. Because the patient's canal diameter is significantly improved, the symptoms of neurogenic claudication should be minimal. It is also conceivable to take a canal diameter that shows moderate stenosis and provide a resection to nearly normal cross-sectional diameter by using the technique described herein. This will provide the patient with less likelihood of progressing to severe stenosis at adjacent levels. It is conceivable that when the spine becomes very stenotic, adjacent segments take on excessive or pathologic movement which can lead to secondary changes such as facet hypertrophy, disk degeneration, and osteophyte formation, etc. Earlier intervention, before severe symptoms occur, therefore provides better spinal integrity.

Figure 1:
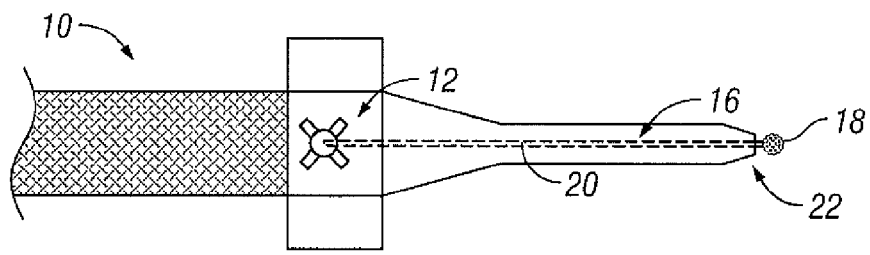
FIG. 1 is an illustration of a surgical drill of the prior art.

In FIG. 1 there is shown a surgical drill of the prior art. One commercially available example of such a device is the Ultrapower™ Surgical Drill System from Hall Surgical. The drill consists of a handpiece 10 connected at its proximal end to a power source, which may, for example, comprise compressed air (not shown). The handpiece 10 has a spindle 12 that rotates in response to actuation of the handpiece motor (not shown), which is driven by the power source. Attached to the front end of the handpiece 10 is a coupling assembly 14. The coupling assembly 14 releasably holds an accessory 16 to the spindle 12 so that the accessory 16 rotates in unison with the spindle 12. The accessory 16, having a rasp or burr 18 at its distal end, is releasably coupled to a handpiece spindle 12. The cutting accessory 16 has a shaft 20, the proximal or rear end of which is releasably held to the spindle 12 by the coupling assembly 14.

The cutting accessory 16 typically extends past the distal tip of the surgical device 22. In this position, it is possible that the burr or rasp 18 could cause unintended injury. For example, because of the power of the tool it is possible that the dura could be pulled into the working channel of the burr or rasp or other resecting instrument. If the neural tissue were pulled into the surgical drill, a neurologic catastrophe could result.

I. The Device

Figure 2A:
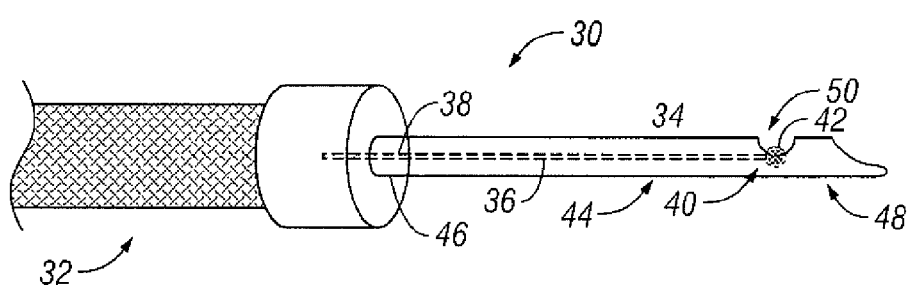
FIGS. 2A-2B are perspective views of the resecting tool in accordance with one embodiment of the present invention, showing the retractor in an "off" and "on" position.
Figure 2B:
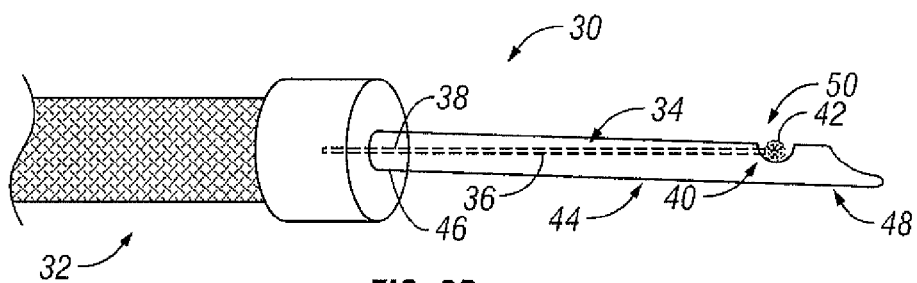

Turning now to FIGS. 2A-2B, there is shown a resecting tool 30 in accordance with one embodiment of the present invention. The resecting tool comprises a handpiece 32, and a resector 34 releasably coupled to the handpiece 32. The resector 34 has a shaft 36 with a proximal end 38 and a distal end 40. At the distal end of the resector 40 is a resecting tip 42. The tip 42 comprises a cutting accessory, such as a rasp or burr. In this embodiment, a burr coupled to the handpiece will be described.

The resecting tool 30 further comprises a retractor 44, in the form of a movable sheath. The retractor 44 has a proximal end 46 and a distal end 48, and an inner and outer surface. The proximal end 46 of the retractor is releasably anchorable near the proximal end of the resector 38. The retractor 44 at least partially surrounds the resector 34, and at least part of the retractor 44 is movable relative to the resector 34. The burr 42 at the distal end of the resector 48 can be fully encased or partially encased at the distal end of the device by the retractor 44. The retractor 44 further comprises an opening 50 at its distal end 48 through which the resecting tip 42 can contact tissue to be resected. This will allow the dorsal aspect of the resecting instrument, in this embodiment the burr 42, to remove bone, ligament, or other tissues without injuring the surrounding tissue, especially the dura, which will be on the ventral side, below the retractor 44. By keeping the dorsal side against the tissue needing to be resected and having the ventral side capable of retracting the surrounding tissue away from the site where resection is occurring, unintended tissue damage is minimized.

During use, a physician may press a foot pedal, button, or other device to start the burr in motion in response to compressed air pressure in the handpiece. This same air pressure can be used to tilt or deflect the retractor body 44 to expose the burr tip. In this embodiment, the same trigger will both start the resection and move the retractor. Alternatively, different triggers could be provided if desired.

The resector itself 34 can include disposable tips that come in a plurality of shapes and sizes. For example such resecting tools may be high-speed burrs or rasps or reamers that can be applied to the power source. Burrs undergo rotational movement and rasps undergo longitudinal movement to remove material, and both of these may be powered with compressed air through the handpiece. Suitable rasps may be essentially conical and have a blunt tip. Alternative sizes may be provided, for example, between 0.5 and 5 mm diameter.

As noted above, these disposable devices are at least partially encased by the retractor that is movable with respect to the resector, and therefore capable of applying pressure to retract, and therefore minimize injury to, vital structures such as nerve roots and blood vessels (epidural veins). The distal end 48 of the retractor preferably extends beyond the distal end 42 of the resector to provide protection distal to the site of the resection. The shape of the retractor can vary so as to accommodate areas in the spinal canal, spinal laminar junction, or into the neural foramen. For example, the distal end 48 of the retractor can be shaped so as to be concave toward the proximal end 46 and flat or convex at the distal end 48. This shape allows the retractor 44 to at least partially surround the length of the resector 34, but also be optimally shaped at the distal end 48 for retraction of the tissue.

Figure 3:
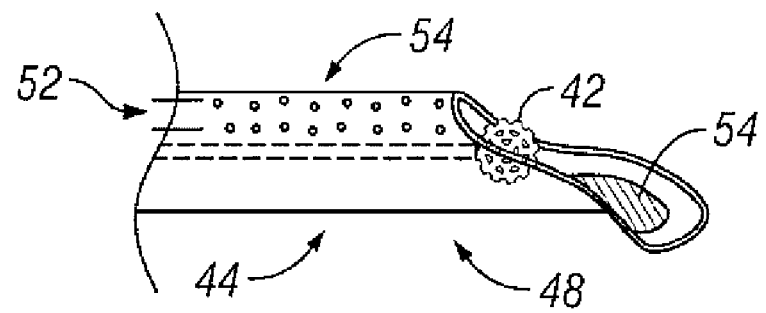
FIG. 3 illustrates the distal end of the resecting tool in accordance with another embodiment of the present invention, wherein the tool includes a separate irrigation and suction channel.
Figure 4:
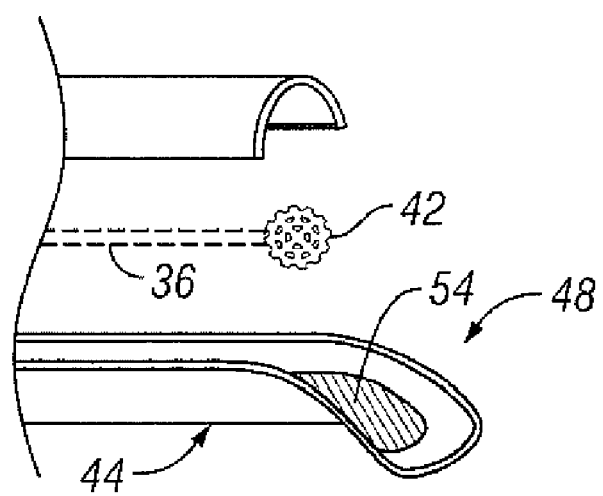
FIG. 4 is an exploded view of the distal end of the resecting tool in accordance with yet another embodiment of the invention.

In another embodiment, illustrated in FIGS. 3 and 4, the distal end of the retractor 48 is shaped so as to be concave toward the proximal end 46 and convex at the distal end 48. Again, the shape is designed to allow the retractor 44 to at least partially surround the length of the resector 34, but also to provide for retraction of the tissue at the distal end 48. "Concave" as used herein includes both cylindrical and semi-cylindrical shapes.

Figure 5A:
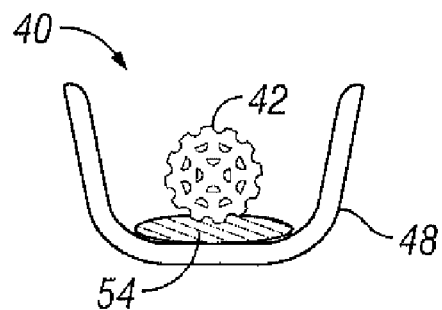
FIGS. 5A and 5B are end views of the distal end of the resecting tool showing the retractor in an "off" and "on" position.
Figure 5B:
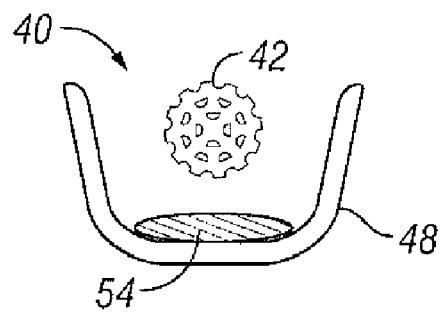

In its "off" or resting position, the distal end of the resector 40 may rest against the inner surface of the distal end of the retractor 48. This is illustrated in FIG. 5A. As shown in FIG. 5B, when the resector is "on," meaning that the burr 42 is rotating, the distal end of the retractor 48 is moved in a downward direction away from the distal tip of the resector 42. This provides for retraction of the tissue away from the burr 42 when it is activated and in motion. To further prevent damage to the tissue of the patient, it is preferable that at least the bottom portion of the inner surface of the distal end of the retractor 48 is provided with a coating of material 54 that is thermally insulating and/or electrically insulating. Such materials include, but are not limited to, ceramics, polyethylene, pyrolytic carbon, biodegradable polylactic acid, polyglycolic acid, polycaprolactone, and copolymers.

II. Other Attachments

In addition to the retractor 44, the resecting tool can also include irrigation and suction capabilities as shown in FIG. 3, which will allow for the removal of detritus and provide for better visualization of the increased cross-sectional diameter of the spinal canal. The suction and irrigation can be provided through a separate channel 52 located within the retractor 44 or as an adjacent cylindrical opening on either side of the retractor (not shown). The hollow conduit 52 will allow for irrigation and also removal of bony or ligamentous detritus. To facilitate delivery of irrigation fluid and/or suction of detritus from the working site, multiple holes 54 may be located at the distal end of the retractor 48.

In addition to irrigation and suction, means for providing illumination at the distal end of the resecting tool can be provided. LEDs, fiberoptic, or other well-known methods for providing illumination to the field can be included.

In addition to illumination, suction and irrigation capabilities, the device can include a camera. The camera can be provided through a separate attachment to the device, or through a separate channel in the device itself. The camera will allow real time imaging of the resection to take place. This allows for the surgeon to directly visualize the procedure as it is being performed. The ability to visualize the resection is vital and provides the surgeon with accurate visualization of the internal laminoplasty, neural foraminal decompression, or removal of disk and/or osteophyte or ligament resection being performed. Such real time imaging will also provide more accurate internal laminoplasty decompression and intraforaminal decompressions to take place without having to resect too little or too much bone. The camera will also facilitate the monitoring and taping of such procedures. This material can then be transmitted to or stored at local or more remote sites.

The collection of such data will allow for a better understanding of spinal stenosis at an earlier stage, and facilitate earlier treatment, which eliminates waiting to have such severe disease or severe clinical symptoms that more extensive open procedures become necessary.

After the resection, bleeding can be controlled by bipolar cautery which can be attached to the retractor after the burr or rasp or other resecting tool is removed. To allow a bipolar cautery for hemostasis, at least a portion of the inner surface of the retractor is preferably made of a nonconducting material as described above. The material can be thermally insulating and/or electrically insulating. Such materials include, but are not limited to, ceramics, polyethylene, pyrolytic carbon, biodegradable polylactic acid, polyglycolic acid, polycaprolactone, and copolymers.

If the electrocautery is not capable of controlling hemostasis, there can be delivered to the site small pieces of hemostatic materials well-known to those in the art, such as Surgicel, microfibrillar collagen, Gelfoam, Fibrillar, FloSeal, Hemaseel, or a variety of other hemostasis materials. In addition, bone wax can be delivered to edges of bone which may continue to bleed. If such bleeding is noted, the use of a variety of different drains can be utilized at the closure of the procedure to prevent hematoma or seromas from building up and causing compression.

In some embodiments, one or more sensors can be utilized as part of the device while the resection is undertaken. The sensors may be capable of sensing pressure or nerve root compression or change in electrical activity. By having this device attached to a computer, information about the spinal canal itself can be stored, processed and transmitted in real time or at a later date.

The sensors can be used to measure pressure or change in electrical activity within a nerve root, or change in physical properties of the surrounding area; e.g., bone vs. ligament vs. epidural vein vs. dura or nerve root sleeves. If the sensors detect a change from bone or ligament at the tip of the resecting tool, a feedback within the system will cause the resecting tool to shut off. In addition, any buildup of ligamentous or bony detritus that is not being suctioned out effectively would also cause the system to shut off.

Figure 6A:
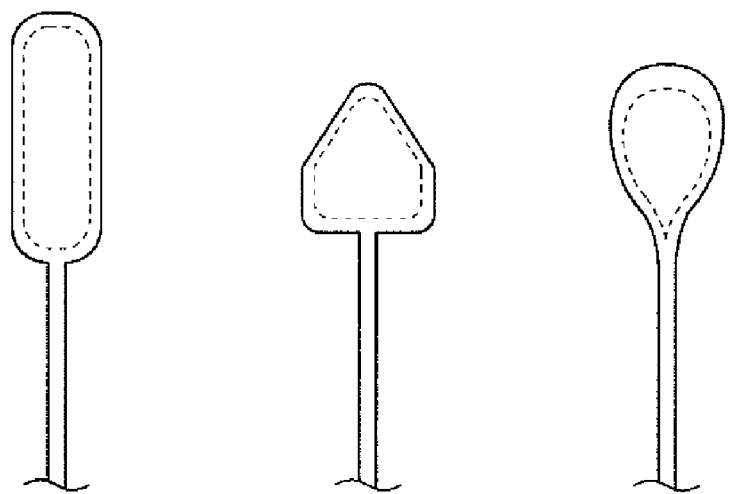
FIGS. 6A and 6B illustrate embodiments of dissection tools and retractor shapes.
Figure 6B:

In addition to the retractor, there may be provided an optional additional dissecting tool that can be used as an extension to provide further separation of the dura from the ligament or the undersurface of the lamina or facets. By freeing up the dura and creating this space it allows the resecting tools to work with impunity in this very tight and delicate area. The additional instrument to free up the dura can be attached to the retractor or be supplied independently such that a dissecting tool is applied to the handpiece in place of the burr/retractor combination. The dissecting tool could be made to tilt or otherwise move in response to footpedal release of compressed air in the handpiece. A variety of shapes, sizes, and are diameters may be provided, as illustrated in FIGS. 6A and 6B. The dissecting tools of FIG. 6A have a variety of shapes and are advantageously configured with slightly blunt and rounded edges. FIG. 6B illustrates a variety of cross sections, which may be used both for the end of the retractor or the end of a dissecting tool. The materials are advantageously biocompatible, which would include but are not limited to, metals such as nitinol, stainless steel, titanium, ceramic, tantalum and other non-biodegradable materials, such as polyethylene, Teflon, pyrolytic carbon, polylactic acid, polyglycolic acid, polycaprolactone, and copolymers.

More elaborate devices acting in concert with the resecting tool can also be introduced to provide more retraction to the thecal sac or nerve root sleeves in the event a more posterolateral decompression is necessary. These retractors may also come in a plurality of sizes and shapes with the ability to bend.

III The Method

Figure 7:
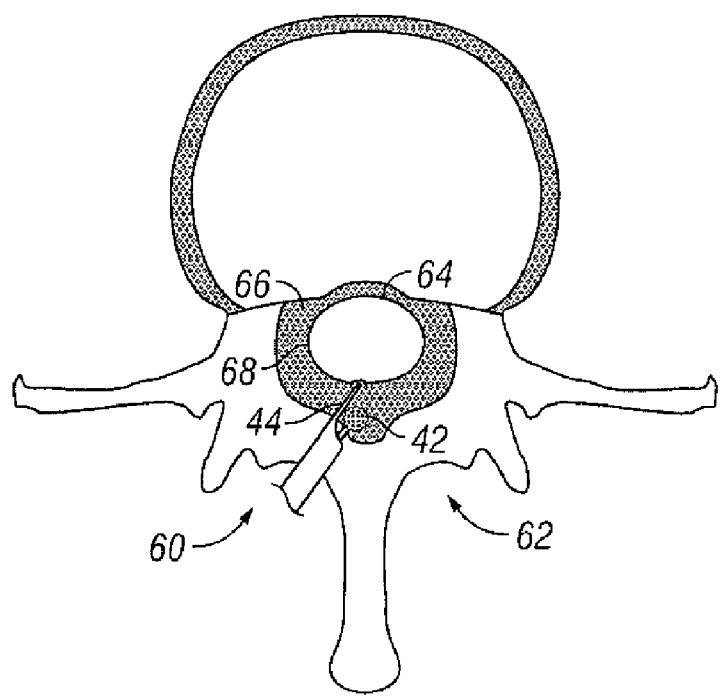
FIG. 7 illustrates the resecting tool of the present invention in use to retract the surrounding tissue away from the site of the resection.

One example of the use of the retractor of the present invention is illustrated in FIG. 7. Generally, the surgeon first performs a minimal incision to the spine. Such an incision would provide access between the interspinous processes down through the interspinous ligament and through the area between the lamina, 60, 62. The spinal cord 64 lies within the vertebral canal 66 and is covered by three membranes, the outermost layer being the dura 68.

The distal end of the resecting tool is delivered to site. During insertion, the tool is in its "off" or resting position, and the distal end of the resector 40 rests against the inner surface of the distal end of the retractor 48, as illustrated in FIG. 5A. When the distal end of the resecting tool is in the desired position, the resector is exposed from within the retractor, and the resector is turned "on" to rotate the burr 42 and to move the distal end of the retractor 48 in a direction away from the distal tip of the resector 42. This provides for retraction of the tissue away from the burr 42 when it is activated and in motion. The burr 42 is used to remove bone, ligament, or other tissues without injuring the surrounding tissue, especially the dura 68, which is on the ventral side of the device, below the retractor 44. By keeping the burr 42 against the tissue needing to be resected and having the retractor 44 retracting the surrounding tissue away from the site where resection is occurring, unintended tissue damage is minimized.

The foregoing description details certain embodiments of the invention. It will be appreciated, however, that no matter how detailed the foregoing appears in text, the invention can be practiced in different ways. As is also stated above, it should be noted that the use of particular terminology when describing certain features or aspects of the invention should not be taken to imply that the terminology is being redefined herein to be restricted to including any specific characteristics of the features or aspects of the invention with which the terminology is associated. The scope of the invention should therefore be construed in accordance with the appended claims and any equivalents thereof.

What is claimed is:

1. A device for osteoligamentous resection comprising:
a resector having a shaft with a proximal end and a distal end, the distal end being defined by a distal tip;
a retractor having a proximal end and a distal end and having an inner surface and an outer surface, the retractor at least partially surrounding the resector, and at least a ventral side of the distal end of the retractor being moveable in a lateral direction relative to and away from the distal end of the resector;
wherein a trigger starts motion of both the resector and the retractor deflecting the retractor body away from and exposing said distal tip of the resector;
a plurality of holes located at the distal end of the resector; and,
wherein at least one of irrigation and suction takes place.

2. A device for osteoligamentous resection comprising:
a resector having a shaft with a proximal end and a distal end, the distal end being defined by a distal tip;
a retractor having a proximal end and a distal end and having an inner surface and an outer surface, the retractor at least partially surrounding the resector, and at least a ventral side of the distal end of the retractor being moveable in a lateral direction relative to and away from the distal end of the resector;
wherein a trigger starts motion of both the resector and the retractor deflecting the retractor body away from and exposing said distal tip of the resector;
at least one of a fiber optic camera and illumination located at the distal end of the resector; and,
wherein at least one of illumination and visualization of the area near the distal end takes place.

* * * * *